United States Patent [19]

Kopolow et al.

[11] 4,423,184

[45] Dec. 27, 1983

[54] SYNTHETIC SUPERABSORBENT FIBERS

[75] Inventors: Stephen L. Kopolow, Plainsboro; Pronoy K. Chatterjee, Spotswood, both of N.J.

[73] Assignee: Personal Products Company, Milltown, N.J.

[21] Appl. No.: 300,086

[22] Filed: Sep. 8, 1981

[51] Int. Cl.$^3$ ............................................ C08F 255/00
[52] U.S. Cl. ..................................... 525/57; 428/378; 428/394; 428/913; 525/61; 604/372; 162/157.4; 162/157.5
[58] Field of Search ............. 162/157 R, 157.4, 157.5; 525/57, 61; 128/284, 296; 604/372; 428/378, 394, 913

[56] References Cited

U.S. PATENT DOCUMENTS

| 3,300,546 | 1/1967 | Baechtold | 525/57 |
| 3,987,139 | 10/1976 | Kozlowski et al. | 162/157 R |
| 4,116,899 | 9/1978 | Fanta et al. | 525/57 |
| 4,340,057 | 7/1982 | Bloch et al. | 128/284 |

FOREIGN PATENT DOCUMENTS 49-12103  2/1974  Japan .............................. 162/157 R Primary Examiner—William F. Smith
Attorney, Agent, or Firm—Jason Lipow

[57] ABSTRACT

Hydrophilic, water retentive synthetic wood pulp fibers are provided which are capable of forming low density fluff. The fibers comprise polyolefins and polyvinyl alcohol wherein the polyvinyl alcohol has, grafted thereto, hydrophilic polymer moieties.

9 Claims, No Drawings

SYNTHETIC SUPERABSORBENT FIBERS

This application relates to absorbent synthetic fibers which are capable of retaining great quantities of fluid and which can be formed into low density fluff for use in such body absorbent products as diapers, tampons, and sanitary napkins.

BACKGROUND OF THE INVENTION

In recent years much effort has been devoted toward producing absorbent materials for use in such body fluid absorbing products such as diapers, catamenial tampons and sanitary napkins. Heretofore, these products have employed naturally occuring cellulose fibers such as wood pulp, cotton and like. In U.S. Pat. No. 3,889,678 issued on June 17, 1975 to Chatterjee et al., a product is disclosed which comprises hydrophilic polymer moieties chemically grafted to the backbone of cellulose fibers. As is disclosed therein, the grafting of these polymer moieties have greatly enhanced the capacity of cellulose fiber systems to absorb and retain body fluids and these grafted materials have proven useful in a wide range of absorbent products. Similar disclosure is found in U.S. Pat. No. 4,105,033 issued on Aug. 8, 1978 to Chatterjee et al.

The above notwithstanding, it has been discovered that while the grafted fibers maintain the general appearance of the starting cellulosic material while providing enhanced absorptive properties, in one respect they behave adversely. Specifically, it has been discovered that grafted cellulose, when combined into pulp fluff exhibits a substantially greater bulk density than the starting cellulosic fibers. This unfortunate property manifests itself when the grafted fibers are produced in board form and subsequently comminuted in a mill or equivalent equipment. It is suspected that the fibers, being somewhat more brittle then wood pulp, for example, tend to crumble and dust to a degree. The resulting pulp fluff exhibits therefore a substantially lower void volume and has a harsher, more abrasive, feel. As a result, the use of the grafted cellulose fiber has been inhibited in certain diaper and sanitary protection products where low bulk density, high void volume and soft feel are desirable for user comfort and protection. Additionally, it has been discovered that the grafted cellulose materials, probably because of their brittleness, do not handle well when attempts are made to process these materials into an absorbent pad. Generally such processing involves an operation such as carding the fibers and when attempts are made to card these brittle fibers, they tend to dust, resulting in inefficient operation and waste. Still further, because these fibers are produced from naturally occurring cellulose fibers, their length is prescribed by nature. Accordingly it is not possible to tailor the length of the fibers to a desired value as is advantageous when attempting to blend these fibers with other fibrous materials. For example, blending is made easier by mixing fibers of comparable length and this optimum way of blending is constrained when employing grafted cellulose made from natural fibers.

For the above reasons, there is a need for a material which is capable of manifesting the high fluid capacity and retention characteristics of the grafted cellulose fibers described above without sacrificing the low bulk density and soft feel of fluffed wood pulp fibers.

SUMMARY OF THE INVENTION

It has now been discovered that a highly absorbent, highly retentive absorbent material may be provided which has all the characteristics of fibrous grafted cellulose but which, unlike such fibrous grafted cellulose, is capable of being comminuted into a low bulk density, high void volume fluff.

Specifically, it has been discovered that by substituting, for the cellulose backbone of the grafted cellulose absorbent described in the aforementioned U.S. Pat. No. 3,889,678, a wholly synthetic polymer, specifically selected in accordance with the teachings herein, a low bulk density product can be obtained. The selection of synthetic material is made by choosing a thermoplastic polymer in admixture with a polymer having sites receptive to accepting hydrophilic polymer moiety grafts. The mixture of choice is a polyolefin, preferably one resulting from the polymerization of olefins having from two to four carbon atoms, i.e., poly(lower olefin), in combination with minor amounts of polyvinyl alcohol. The grafted moiety of choice is selected from the group of poly (carboxylic acid) type polymers, preferably hydrolyzed to their alkali salts.

The resulting products have fluff densities of less then about 0.03 gm/cc which is essentially the fluff density of the starting synthetic polymer fibers before grafting.

DETAILED DESCRIPTION OF THE INVENTION

The low bulk density absorbent materials of this invention comprise synthetic polymeric materials onto which are grafted hydrophilic carboxylic polymer moieties.

The synthetic polymer materials providing the backbone for the grafts are preferably those which are known in the art as synthetic wood pulp and have physical and morphological properties similar to wood pulp fibers. Typical of such are the synthetic wood pulp fibers formed from polyolefins e.g., polyethylene and polypropylene such as were sold by Crown Zellerback, a corporation of Nevada, under the trademark, SWP, and is now sold by Crown Zellerback under the trademark FYBREL Synthetic Fiber.

Various methods for making synthetic wood pulp are known, including (1) solution polymerization accompanied by stirring, (2) dissolving a preformed polymer and subjecting the solution to an anti-solvent, or (3) forming the polymer at the interface between liquid layers, with localized stirring provided to pull the polymeric material thus produced into fibrillated forms. Examples of methods for producing synthetic wood pulp fibers are disclosed in U.S. Pat. Nos. 3,560,318; 3,081,519; 3,003,912; 3,068,527, and 3,290,209; South Africa Pat. No. 69/7 431; U.K. Pat. No. 1,102,342 and Dutch Patent App. No. A132/48-7313178.

Morphologically, the synthetic wood pulp fibers generally are sized and shaped to resemble naturally occurring wood pulp fibers being elongated, supple, randomly bent and having an irregular cross section at any given point along the length of the fiber, said cross section also varying from point to point along the fiber length. The predominant shape of the fiber is usually ribbon-like.

The synthetic wood pulp fibers are predominantly comprised of hydrophobic polymers and specifically lower polyolefins such as polyethylene and polypropylene. A degree of hydrophilicity is imparted to these fibers by incorporating, in physical admixture, small proportions of hydrophilic polymers such as, for example, small quantities of polyvinyl alcohol. For example, the SWP fibers manufactured by the Crown Zellerbach Corporation are available in several grades containing from 0.8 to 4.0%, by weight, polyvinyl alcohol. The incorporation of these hydrophilic polymers tends to bring the absorbent properties of the SWP within an order of magnitude to that of wood pulp. This notwithstanding, the SWP fibers fall far short of wood pulp in their ability to absorb and retain fluids and, of course, are substantially less effective then the grafted cellulose fibers described above.

In accordance with the teachings herein, it has been discovered that advantage can be taken of the presence of these intermixed hydrophilic polymers by utilizing them as sites for graft co-polymerization of further polymer moieties to produce a product having the desired levels of absorbent capacity and fluid retention. Surprisingly, it has been discovered that this may be accomplished while maintaining essentially the same low bulk density of the starting synthetic wood pulp materials.

The starting material is therefore synthetic wood pulp comprising lower polyolefins, i.e., two to four carbon atoms, and small qualities of hydrophilic polymers. Preferably, fibers of polyethylene or polypropylene are employed in combination with small quantities of polyvinyl alcohol. The polyvinyl alcohol is preferably present in the range of about 0.5% by weight based on the weight of the poly(olefin) and the poly(vinyl alcohol). Preferably, the polyvinyl alcohol is present in quantities of at least about 0.8%, by weight. This starting material is then modified by grafting hydrophilic chains of the general formula (I):

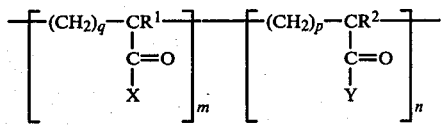

wherein $R^1$ and $R^2$ are selected from the group consisting of hydrogen and alkyl having 1 to 4 carbon atoms, X and Y are selected from the group consisting of —OH, —O(alkali metal), and —NH$_2$, wherein m is an integer having a value of zero to about 5000, n is an integer having a value of zero to about 5000, the total number of m and n moieties on a chain is at least 500, p is an integer having a value of zero or 1, and q is an integer having a value of 1 to 4.

Preferred hydrophilic chains are those selected from the group consisting of poly(acrylic acid), alkali poly(acrylate), such as sodium or potassium poly(acrylate) and copolymers of these which may be obtained, for example, by the hydrolysis of poly(acrylonitrile) chains. It should be understood that in the hydrolysis of poly(acrylonitrile) chains, some poly(acrylamide), an intermediate product, is formed and may be also present in the final product.

While the detailed mechanism by which the grafting of the hydrophilic chain or chains onto a polymeric backbone is not fully known, it is believed that one possibility is that grafting takes place through a free radical mechanism whereby the free radical is situated on the polymeric backbone which serves as a reducing agent and the hydrophilic chain is attached to the polymeric reducing agent through a carbon linkage to produce the graft copolymer.

The hydrophilic chains are polymers of an olefinically unsaturated carboxylic acid or a derivative thereof with itself or with at least one other monomer copolymerizable therewith. The resulting polycarboxylic acid-type polymers can, for example, include those containing monomer units such as acrylic acid, acrylic anhydride, methacrylic acid, crotonic acid, maleic acid, itaconic acid, citraconic acid, alpha-dimethyl maleic acid, alpha-butyl maleic acid, fumaric acid, aconitic acid, as well as partial salts, amides and esters thereof. Anhydrides of any of the aforesaid acids can also be employed.

The initial copolymers of anhydrides with another monomer can be converted to carboxyl-containing copolymers by reaction with water, and carboxylate-containing moieties, such as ammonium or metal compounds such as sodium hydroxide, potassium hydroxide, and the like or with aqueous ammonia.

The copolymers are formed in a known manner by reacting admixtures of the desired monomers in the presence of an initiator in a suitable solvent for the monomers.

The obtained copolymers are conveniently identified in terms of their monomeric constituents. However, the names so applied to the copolymers refer to the molecular structure of the polymer and are not limited to the polymers prepared by the copolymerization of the specific monomers. In many instances, the identical copolymers may be prepared from other monomers and converted to the desired copolymer by a subsequent chemical reaction.

A preferred hydrophilic polymer chain can be prepared by several methods known in the art. Illustrative of such methods are the following:

(1) Polymerize acrylonitrile and hydrolyze with an alkaline solution to form alkali salts or polyacrylic acid.
(2) Polymerize acrylic acid or alkali salts or acrylic acid.
(3) Polymerize methacrylonitrile and hydrolyze with acids to form polymethacrylic acid or hydrolyze with an alkaline solution to form alkali salts of polymethacrylic acid.
(4) Polymerize methacrylic acid or alkali salts of methacrylic acid.
(5) Polymerize acrylamide, optionally followed by hydrolysis.
(6) Polymerize methacrylamide, optionally followed by hydrolysis.
(7) Form copolymers of any of the above monomers.

Methods of graft-copolymerizing olefinically-unsaturated chains onto cellulose are known in the art and may be employed in connection with this invention. Thus, grafting of the hydrophilic material onto the synthetic wood pulp can be accomplished simultaneously with the formation of the hydrophilic polymeric material in an aqueous medium, because the initiators used to copolymerize the various monomers forms a redox system and thus also serves to effect chain transfer onto the cellulose. Suitable initiators for this purpose are ceric ion, ferrous ion, cobaltic ion, (NH$_4$)$_2$S$_2$O$_8$, cuprous ion, and the like. The desired ions can be supplied in the form of salts such as ceric ammonium nitrate, ferrous ammonium sulfate, and the like. Graft-copolymerization of olefinically-unsaturated chains can also be effected by irradiation (ultra-violet-, electron beam-, gamma-or X-radiation) or by heating in an aqueous medium in the presence of an emulsifier.

The synthetic wood pulp fibers can be slurried in water containing a graft-copolymerization initiator system and the monomer or monomers added to the slurry and polymerized in situ at ambient temperature or above depending on the initiator employed.

Hydrophilic chain loading on to the synthetic wood pulp can vary from about 10 percent by weight to about 90 percent by weight, and preferably is about 40 to about 80 percent by weight of the grafted synthetic wood pulp product.

The preferred polymer moieties are at least partially hydrolyzed acrylic polymers. Hydrolyzed copolymers of acrylontrile and ethylacrylate are the polymers of choice. The copolymerization and grafting reaction are preferably initiated using a ceric ion initiator at an acidic pH, e.g. about 0.8 to about 2.3, and at room temperature. Because the reaction is inhibited by the presence of oxygen, it is desirable to flush out essentially all the oxygen from the reaction system by bubbling therethrough non-oxidizing gas such as nitrogen, helium, argon, etc.

The grafted moieties are hydrolyzed by reacting the fibers, preferably under reflux, with an excess of a strong base solution e.g. sodium hydroxide. The concentration of this solution may be from about 1% to about 5% by weight.

The resulting product is washed free of reactants and dried. Drying may be accomplished using heated air but, preferably, physical and absorbent properties are best preserved by using methods such as freeze drying or solvent extraction, as are known in the art. Freeze drying may be accomplished by methods well known in the art which comprise subjecting the wet material to temperatures below the freezing point of the liquid and then removing the frozen liquid by sublimation, this being accomplished by subjecting the frozen material to subatmospheric pressures and withdrawing the sublimated vapors. Solvent extraction is also known in the art and comprises dispersing the wet material in a volatile solvent in which the water held by the solvent is soluble to an appreciable extent. The volatile solvent is then removed by evaporation into heated air.

The dried fibers are fluffed, by mechanical agitation to produce a low density fluff. Such fluff has a density comparable to that of both unmodified wood pulp fluff and unmodified synthetic wood pulp i.e. in the order of from about 0.01 to about 0.05 grams/cc. At the same time the grafted synthetic wood pulp has a minimum fluid capacity (as defined by the Porous Plate Test described hereafter) of at least 1.5 times that of wood pulp fluff and more than five times that of unmodified synthetic wood pulp. Similarly, with respect to fluid retention (as also defined herein) the low density grafted synthetic wood pulp exhibits retentions of more than 6 times that of wood pulp and 12 times that of unmodified synthetic wood pulp.

EXAMPLE I

Into a three-necked flask fitted with a stirrer, a gas bubbling tube and a stopped funnel are placed 1000 ml of water and 20 grams SWP fibers obtained from the Crown Zellerbach Corporation and designated by them as E-830. Such fibers have a length of about 1.3 to 1.8 mm, and consists of polyethylene and polyvinyl alcohol wherein the polyvinyl alcohol is present in an amount of approximately 4.0%, by weight. The suspension is deaerated by bubbling dry nitrogen through the system for fifteen minutes while continually stirring. To the stirred suspension is added 24 ml of a ceric ammonium nitrate initiator solution while continuing the nitrogen purging. The ceric ammonium nitrate initiator solution is prepared by dissolving the ceric salt in 1 N nitric acid to a concentration of 10 millimoles per 100 ml of solution.

After complete dispersion of the initiator, a mixture of 31.8 gm of acrylonitrile and 55.4 gms of ethyl acrylate is added and the system is allowed to react for two hours at room temperature.

The resulting grafted fibers are now isolated by being transferred to a Buchner funnel and washed thoroughly with water. The washed fibers are then hydrolyzed with an excess of 6% sodium hydroxide solution for 30 minutes at reflux temperature. The resulting hydrolyzed product is next washed with water until the wash water has a pH of 7 to 8. The wet material is then spread on a tray and frozen at a temperature of $-25°$ C. in a freezer. The frozen material is then placed in a Cryolizer Freeze Drying Apparatus manufactured by the New Brunswick Scientific Company (Model No. B64) and freeze dried at equilibrium temperature and under a vacuum of between 0 to 5 microns of mercury. The dried product is next fluffed in a Waring blender (Model No. 12BL3) by stirring for 45 seconds at a setting of seven (mix setting), which results in a low density absorbent fluff.

EXAMPLE II

The method of producing grafted SWP set out in Example I is followed with the exception that the ratio of pulp to total monomer is varied while keeping the ratio of each monomer to the other constant to obtain various degrees of grafted polymer add-on. Grafted polymer add-on is defined as 100 times the difference between the weight of the bone dry finished material and the starting pulp divided by the weight of the finished material.

Additionlly, samples made in accordance with the method described in U.S. Pat. No. 3,889,678 are produced having various grafted polymer add-on and differing from the grafted SWP in that the starting material is wood pulp. These samples are tested for absorbency, i.e., both maximum capacity and fluid retention, utilizing the Porous Plate Testing apparatus, as described in detail in Textile Res. J., 37 pp 356–366, 1967. Briefly, this test involves placing the sample fluff in what is essentially a Buchner funnel having a porous bottom plate and holding the sample in place by applying thereon a standard weight to maintain a standardized confining pressure. The porous plate is placed in contact with a reservoir of fluid and the sample is allowed to absorb fluid through the porous plate until saturated. By maintaining the samples at essentially the level of the reservoir, the fluid absorbed is subjected to essentially zero hydraulic head with respect to the reservoir. The volume of the absorbed fluid, divided by the weight of the sample, is termed the Maximum Capacity. To determine fluid retention, the saturated sample is elevated with respect to the fluid reservoir, thereby imposing a hydraulic head upon the fluid absorbed, the head being arbitrarily chosen as 35.5 cm of fluid. The apparatus is provided with means for measuring the volume of fluid retained under the hydraulic head. Retention values are reported as the volume retained per unit weight of sample. The results of testing various samples of the material of the grafted synthetic wood pulp (GSWP) and the materials of U.S. Pat. No. 3,889,678, grafted wood pulp (GWP), are illustrated in Table I, below. The test fluid used is a 1% by weight, aqueous NaCl solution.

TABLE I

| POROUS PLATE TEST | | | | | |
|---|---|---|---|---|---|
| GSWP | | | GWP | | |
| Polymer add-on (%) | Absorbency (cc/g) | | Polymer add-on (%) | Absorbency (cc/g) | |
| | Maximum Capacity | Retention | | Maximum Capacity | Retention |
| 31 | 13.2 | 9.1 | — | — | — |
| 52 | 17.4 | 11.7 | 55 | 14.0 | 6.5 |
| 64 | 17.5 | 12.8 | — | — | — |
| 69 | 24.6 | 16.0 | 80 | 17.0 | 12.0 |

As can be seen from the above table, at essentially comparable polymer add-on percentages, the grafted synthetic wood pulp exhibits significantly greater absorbency properties over that of the grafted wood pulp.

EXAMPLE III

The procedures of Example I are employed with the exception that the acrylonitrile and ethylacrylate monomer are introduced in a 1 to 1 molar ratio and SWP fibers having various proportions of polyvinyl alcohol are used. The Maximum Capacity of these samples is determined using the method described above as well as the weight percent conversions (i.e., percent polymerization) of the monomers. Table II below gives these results.

TABLE II

| VARYING POLYVINYL ALCOHOL (PVA) | | | |
|---|---|---|---|
| Sample | PVA (% by wt.) | Maximum Capacity (cc/g) | Monomer Conversions (% by wt.) |
| 1 | 0.8 | 5.0 | 22.5 |
| 2 | 2.0 | 5.0 | 39.0 |
| 3 | 3.0 | 6.9 | 39.5 |
| 4 | 4.0 | 11.9 | 58.0 |

As can be seen from the above table, both the maximum capacity as well as the monomer conversion increase with increasing polyvinyl alcohol content.

EXAMPLE IV

The procedures of Example I are followed to prepare samples wherein the polyvinyl alcohol content is held constant at 4% by weight and the molar ratio of acrylonitrile to ethylacrylate monomer is varied. Again, both maximum fluid capacity and monomer conversion are determined as described in the preceding example. The results are reported in Table III below.

TABLE III

| VARYING MONOMER RATIOS | | | |
|---|---|---|---|
| Sample | Monomer Ratio (molar) | Maximum Capacity (cc/g) | Monomer Conversions (% by wt.) |
| 5 | 0 | 0.2 | 0 |
| 6 | 0.5 | 4.0 | 39 |
| 7 | 1.0 | 11.9 | 57 |
| 8 | 2.0 | 9.0 | 45 |
| 9 | 3.0 | 8.9 | 44 |

As can be seen from the above table, both the maximum capacity as well as the monomer conversion are highest at a monomer ratio of 1.0.

EXAMPLE V

A series of samples are fluffed in accordance with the method of Example I and measured to determine the bulk density of the fluff material as well as the absorption properties. Sample 1 is a wood pulp sample, sample 2 is a sample of the SWP fiber described in Example I and having a weight percent polyvinyl alcohol content of 4%. Sample 3 is the GWP sample of Example I having a polymer add-on of 80%. Samples 4 and 5 are the grafted SWP of this invention and, specifically the sample identified as sample 4 in Example III. Sample 4 varies from sample 5 in that the former is freeze dried and the latter is dried by solvent extraction. The freeze drying is carried out following the procedure of Example I. Solvent extraction is accomplished by first water washing the wet hydrolyzed material to a pH of 7 to 8. The washed material is then dispersed in acetone, in a ratio of 100 grams of wet material to a liter of acetone, and then filtered. The filter cake is then dried in an air circulated oven at 80° C. All samples are fluffed as described in Example I. The results of the density determinations and absorbency tests are reported in Table IV below.

TABLE IV

| DENSITY/ABSORBENCY COMPARISON | | | | |
|---|---|---|---|---|
| | | | Absorbency (cc/g) | |
| Sample | Type | Density (g/cc) | Max. Capacity | Retention |
| 1 | Wood Pulp | 0.030 | 12 | 2 |
| 2 | SWP | 0.024 | 2 | 1 |
| 3 | GWP | 0.160 | 18 | 13 |
| 4 | GSWP (freeze dried) | 0.015 | 19 | 13 |
| 5 | GSWP (solvent extr) | 0.020 | 22 | 16 |

As can be seen from this table, the ungrafted starting materials, wood pulp and SWP, both have essentially the same low bulk density and low retention properties. Wood pulp, being more hydrophilic, exhibits a substantially higher maximum capacity. Upon grafting the wood pulp, the resulting GWP sample exhibited a marked increase in both maximum capacity and fluid retention and, unfortunately, a concomitant increase in bulk density. Similarly, upon grafting the SWP to produce the GSWP sample, both samples 4 and 5 showed marked increases in absorptive properties exceeding that of the grafted wood pulp samples. In contrast to the grafted wood pulp, however, the grafted synthetic wood pulp of this invention exhibited low bulk densities, comparable to that of the starting materials.

What is claimed is:

1. Hydrophilic, water retentive synthetic wood pulp fibers capable of forming low density fluff and comprising polyolefin and polyvinyl alcohol, said polyvinyl alcohol having grafted thereto hydrolyzed ethylene acrylate acrylonitrile copolymer, said fibers having been freeze dried.

2. Hydrophilic, water retentive synthetic wood pulp fibers capable of forming low density fluff and comprising polyolefin and polyvinyl alcohol, said polyvinyl alcohol having grafted thereto hydrolyzed ethylene acrylate acrylonitrile copolymer, said fibers having been solvent dried.

3. The fibers of claim 1 or 2 wherein said polyvinyl alcohol is present in a quantity of at least about 0.5 percent by weight based on the weight of the polyolefin and the polyvinyl alcohol.

4. The fibers of claim 3 wherein said polyvinyl alcohol is present in a quantity of at least about 0.8 percent by weight, based on the weight of the poly(olefin) and the vinyl alcohol.

5. The fibers of claim 1 or 2 wherein the poly(olefin) comprises polyethylene.

6. The fibers of claim 1 or 2 wherein the poly(olefin) comprises polypropylene.

7. The fibers of claim 1 or 2 wherein said hydrolyzed ethylene acrylate acrylonitrile copolymer comprises from about 10 percent by weight to about 90 percent by weight of said grafted synthetic wood pulp fiber.

8. The fibers of claim 7 wherein said hydrolyzed ethylene acrylate acrylonitrile copolymer comprises from about 40 percent by weight to about 80 percent by weight of said grafted synthetic wood pulp fibers.

9. The fibers of claim 1 or 2 in the form of a low density fluff having a density of from about 0.01 to about 0.05 grams per cc.

* * * * *